(12) United States Patent
Loessel et al.

(10) Patent No.: US 8,710,254 B2
(45) Date of Patent: Apr. 29, 2014

(54) METHOD FOR PRODUCING ORGANO-OLIGO SILSESQUIOXANES

(75) Inventors: Georg Loessel, Emmerting (DE); Manfred Meisenberger, Burghausen (DE)

(73) Assignee: Wacker Chemie AG, Munich (DE)

( * ) Notice: Subject to any disclaimer, the term of this patent is extended or adjusted under 35 U.S.C. 154(b) by 185 days.

(21) Appl. No.: 13/501,962

(22) PCT Filed: Oct. 6, 2010

(86) PCT No.: PCT/EP2010/064924
§ 371 (c)(1),
(2), (4) Date: Apr. 13, 2012

(87) PCT Pub. No.: WO2011/045218
PCT Pub. Date: Apr. 21, 2011

(65) Prior Publication Data
US 2012/0203019 A1 Aug. 9, 2012

(30) Foreign Application Priority Data
Oct. 14, 2009 (DE) .......................... 10 2009 045 669

(51) Int. Cl.
*C07F 7/20* (2006.01)
(52) U.S. Cl.
USPC ............................ 556/462; 556/470; 556/482
(58) Field of Classification Search
USPC .......................................... 556/462, 470, 482
See application file for complete search history.

(56) References Cited

U.S. PATENT DOCUMENTS

| 5,047,492 A * | 9/1991 | Weidner et al. ................. 528/15 |
| 5,204,432 A | 4/1993 | Saito et al. |
| 5,442,025 A * | 8/1995 | Spes et al. ........................ 528/15 |
| 2005/0010012 A1 * | 1/2005 | Jost et al. ......................... 528/34 |
| 2005/0142054 A1 | 6/2005 | Hasegawa et al. |

FOREIGN PATENT DOCUMENTS

| DE | 3837397 A1 | 5/1990 |
| DE | 10156619 A1 | 5/2003 |
| EP | 0446912 A1 | 9/1991 |
| JP | 01-266137 A | 10/1989 |
| JP | 2008266248 A | 11/2008 |

OTHER PUBLICATIONS

D. Hoebbel and W. Wieker "Die Konstituion des Tetramethylammoniumsilicate der Zusamnnensetzung . . . " Z. Anorg. Allg. Chem., 384, 43-52 (1971).
I. Hasegawa and S. Sakka "The Effect of Tetramethylammonium Ions on the Distribution of Silicate Species in the Methanolic Solutions", Journal of Molecular Liquids, 34 (1987) 307-315.

* cited by examiner

*Primary Examiner* — Johann R Richter
*Assistant Examiner* — Pancham Bakshi
(74) *Attorney, Agent, or Firm* — Brooks Kushman P.C.

(57) ABSTRACT

Silsesquisiloxanes are produced in high yield and purity in a minimal number of process steps by reacting quaternary ammonium silicates with disiloxanes in a precipitant liquid which causes the silsesquisiloxane product to be precipitated in high purity.

12 Claims, No Drawings

METHOD FOR PRODUCING ORGANO-OLIGO SILSESQUIOXANES

CROSS-REFERENCE TO RELATED APPLICATIONS

This application is the U.S. national phase of PCT Appln. No. PCT/EP2010/064924 filed Oct. 6, 2010, which claims priority to German Patent Application No. 10 2009 045 669.4 filed Oct. 14, 2009, which are incorporated herein by reference.

BACKGROUND OF THE INVENTION

1. Field of the Invention

The invention relates to a method for producing organooligosilsesquioxanes from silicates and disiloxane compounds.

2. Description of the Related Art

Organooligosilsesquioxanes are useful as crosslinking agents for silicones and organic polymers.

DE 38 37 397 A1 and also DE 101 56 619 A1 disclose organooligosilsesquioxanes and methods for producing them. In DE 38 37 397 A1 such organooligo-silsesquioxanes are preferably produced by the reaction with a reactant in excess as a solvent for the reaction product.

Furthermore, examples 8 and 9 of DE 38 37 397 describe a production method which, from the start of silicate production to obtaining the pure reaction product, constitutes a 6-step manufacturing process:

first, producing the silicate base by reacting precipitated silica with aqueous tetramethylammonium hydroxide solution;

second, concentrating the reaction mixture and crystallizing the tetramethylammonium silicate product at 4° C.;

third, reacting tetramethylammonium silicate with a reactant used in excess and acting as solvent for the organooligosilsesquioxane;

fourth, phase separating and washing the organic phase until neutral;

fifth, evaporating the washed neutral reaction mixture to dryness; and sixth, recrystallizing the residue from an alcohol.

Thus, DE 38 37 397 A1 describes a production method having unavoidably high cost requirements and relatively poor yields (of 60-70%) in order that high-purity organooligosilsesquioxanes may be produced.

SUMMARY OF THE INVENTION

The invention provides a method for producing organo-oligosilsesquioxanes of general formula (I)

$$[RSiO_{3/2}]_z \quad (I)$$

where

R represents moieties of general formula (II)

$$-O-SiR^1_2Y \quad (II),$$

by reaction of 100 mol of silicates of general formula (III)

$$(W_4NOSiO_{3/2})_z \quad (III),$$

with not more than 1.3×50×z mol of disiloxane compounds of general formula (IV), $$R^1_2YSi-O-SiR^1_2Y \quad (IV),$$

where $R^1$ represents a divalent $C_1$- to $C_6$-hydrocarbon or $C_1$- to $C_6$-alkoxy moiety, Y represents a hydrogen atom or a halogenated or nonhalogenated $C_1$- to $C_H$-hydrocarbon moiety, W represents a $C_1$- to $C_4$-alkyl moiety, and z represents the number 6, 8 or 10, in the presence of a precipitant which is liquid at reaction temperature and in which at reaction temperature at most 1 g of organooligosilsesquioxanes of general formula (I) are soluble in 100 ml of precipitant.

BRIEF DESCRIPTION OF THE PREFERRED EMBODIMENTS

The method which the invention provides for producing organooligosilsesquioxanes of general formula (I) is a precipitation reaction wherein none of the reactants acts as solvent for the resultant organooligosilsesquioxane of general formula (I). Therefore, the product of general formula (I) crystallizes out in the reaction medium at a high purity of 95-100%, especially of 99-100%, measured via $^1$H NMR, directly after the reaction. Organooligosilsesquioxanes of general formula (I) are preferably generated as colorless powders. High yields of not less than 70%, based on employed silicates of general formula (III), are attainable.

The method is simple and economical. The method according to the present invention eliminates technically involved process steps of the kind described in the prior art, such as phase separation, washing, drying, recrystallization.

The production process according to the present invention can be run as a batch operation, as a semibatch operation and/or as a continuous process.

R may represent identical or different moieties depending on the choice of identical or different, symmetrical or asymmetrical disiloxane compounds of general formula (IV). It is particularly preferable for R to represent —O—Si(CH₃)₂H or —O—Si (CH₃)₂H₃C₂.

$R^1$ is preferably methyl, ethyl, phenyl, methoxy, ethoxy or propoxy.

Y is preferably methyl, phenyl or a $C_2$- to $C_{10}$-alkenyl moiety which preferably has only one double bond, especially a vinyl or allyl group. Further preferred Y moieties are $C_1$- to $C_{10}$-alkyl moieties that have a halogen atom, such as chlorine or bromine, on the terminal carbon atom, especially 3-chloropropyl, 3-bromopropyl, 6-chlorohexyl.

W is preferably methyl, ethyl or n-propyl.

Preferably not more than 1.2×50×z molar parts, more preferably not more than 1.1×50×z molar parts and even more preferably not more than 1.05×50×z molar parts of disiloxane compounds of general formula (IV) are used per 100 molar parts of silicates of general formula (III). Preferably not less than 0.3×50×z molar parts, more preferably not less than 0.8×50×z molar parts and even more preferably not less than 0.95 ×50×z molar parts of disiloxane compounds of general formula (IV) are used per 100 molar parts of silicates of general formula (III).

The reaction temperature is preferably not less than 0° C., and especially not less than 20° C. and preferably not more than 100° C., more preferably not more than 60° C. and especially not more than 40° C.

The reaction is preferably carried out at the pressure of the ambient atmosphere, i.e., about 0.1 MPa (abs.). However, it can also be carried out at higher or lower pressures. Preference is given to pressures of not less than 0.08 MPa (abs.), more preferably not less than 0.09 MPa (abs.), yet more preferably not more than 0.2 MPa (abs.) and most preferably not more than 0.15 MPa (abs.).

The precipitants are liquid at reaction temperature, especially at 25° C. and 0.1 Mpa. The precipitant also serves as diluent in the reaction. Solvents or solvent mixtures having a boiling point or boiling range of up to 120° C. at 0.1 MPa are preferred as precipitants. Preferred precipitants are polar solvents such as water; alcohols such as methanol, ethanol, n-propanol, isopropanol or butanol; ethers such as dioxane, tetrahydrofuran, diethyl ether, diethylene glycol dimethyl ether; chlorinated hydrocarbons such as dichloromethane, trichloromethane, 1,2-dichloroethane, trichloroethylene; ketones such as acetone; lactones such as 4-butyrolactone; nitriles such as acetonitrile; nitro compounds such as nitromethane; tertiary carboxamides such as dimethylformamide; urea derivatives such as tetramethylurea or dimethylpropyleneurea (DMPU); sulfoxides such as dimethyl sulfoxide (DMSO); sulfones such as sulfolane; carbonic esters such as dimethyl carbonate or ethylene carbonate; carbon sulfide and nitrobenzene; primary and secondary amines such as diethylamine; carboxylic acids such as formic acid or acetic acid; primary and secondary amides, such as formamide; mineral acids, such as sulfuric acid, nitric acid, phosphoric acid, hydrochloric acid, and boric acid; or mixtures thereof.

The method according to the present invention is preferably carried out in a polar protic solvent. Water and alcohols are preferred for this.

It is preferable for not more than 0.5 g and especially for not more than 0.1 g of organooligosilsesquioxanes of general formula (I) to be soluble in 100 ml of precipitant at reaction temperature.

The method according to the present invention is preferably carried out in the presence of an acidic catalyst. The catalyst and the amounts in which it is used are known from the prior art. Per 100 mol of silicates of general formula (III) it is preferable to use not less than 0.01 mol, more preferably not less than 0.1 mol, yet more preferably not less than 0.5 mol and most preferably not less than 5 mol of catalyst, and not more than 200 mol, more preferably not more than 100 mol and especially not more than 50 mol of catalyst.

Examples of such acidic catalysts are acids, especially Lewis acids such as $BF_3$, $AlCl_3$, $TiCl_4$, $SnCl_4$, $SO_3$, $PCl_5$, $POCl_3$, $FeCl_3$ and its hydrates, $ZnCl_2$ and phosphorus nitride chlorides; Brönstedt acids such as hydrochloric acid, hydrobromic acid, sulfuric acid, chlorosulfonic acid, phosphoric acids such as ortho-, meta- and polyphosphoric acids, boric acid, selenous acid, nitric acid, acetic acid, propionic acid, haloacetic acids, such as trichloro- and trifluoroacetic acid, oxalic acid, p-toluenesulfonic acid, acidic ion exchangers, acidic zeolites, acid-activated fuller's earth, acid-activated carbon black, hydrogen fluoride, hydrogen chloride, and the like. Hydrochloric acid is particularly preferred.

The production of silicates of general formula (III) is known in the prior art and described for example by D. Hoebbel and W. Wieker (Zeitschrift für anorganische und allgemeine Chemie 384, pages 43-52 (1971)) and I. Hasegawa and S. Sakka (Journal of Molecular Liquids 34, pages 307-315 (1987)). Preparation is possible for example by hydrolysis of tetraethyl silicate in aqueous methanol in the presence of tetraalkylammonium hydroxides, in which case suitable choice of the tetra-alkylammonium hydroxide and of the weight ratios of the reactants provides a way of selectively preparing molecules of formula (III) for which z represents 6, 8 or 10.

In one preferred embodiment, in a first step, the silicates of general formula (III) are produced in a solution of $W_4N^+ OH^-$ in the precipitant, especially water, methanol or mixtures thereof, with tetraalkoxysilanes where the alkoxy moieties have 1 to 6, especially 1, 2 or 3 carbon atoms. The mixture thus produced can then be used directly as a crude product in the method according to the invention.

This is an immense simplification of the process, since the silicates of general formula (III) can be used without prior purification by recrystallization.

In a further preferred embodiment, the co-produced salt composed of tetraalkylammonium cation and anion from the catalyst $W_4N^+ A^-$, especially tetramethylammonium chloride, is separated off and regenerated with alkali or alkaline earth metal hydroxide, preferably with alcoholic, for example methanolic, KOH solution to $W_4N^+ OH^-$, especially tetraalkylammonium hydroxide. The $W_4N^+ OH^-$ can then be reused for the production of silicates of general formula (III).

The organooligosilsesquioxanes of general formula (I) that are obtainable via the method according to the present invention are useful as crosslinking agents for polymers, especially for silicones.

All foregoing symbols of foregoing formulae each have their meanings independently of each or one another. The silicon atom is tetravalent in all formulae.

All above-recited reaction participants and auxiliary chemicals can be used singly or mixed.

EXAMPLES

In the examples hereinbelow, unless otherwise stated in each case,
a) all quantities are by weight;
b) all pressures are 0.10 MPa (abs.);
c) all temperatures are 20° C.

Example 1 (Corresponds to Example 8 of DE 38 37 397 A1, and is Not in Accordance with the Present Invention)

Synthesis of octa(vinyldimethylsiloxy)octasilsesquioxane $[(H_2C=CH)(CH_3)_2SiOSiO_{3/2}]_8$ a) 82.2 g of precipitated silica were admixed with 1250 ml of 10% strength aqueous tetramethylammonium hydroxide solution (TMAOH).

The mixture was stirred for 16 h at 25° C. and for 8 h at 50° C. to obtain a clear solution. The solution was concentrated to two-thirds of its initial volume and the tetramethylammonium silicate content crystallized at 4° C. to obtain 359.5 g of still water-containing tetramethylammonium silicate.

b) 160 g of this tetramethylammonium silicate were added a little at a time to an efficiently stirred mixture of 450 ml of $H_2O$, 1000 ml of isopropanol, 1700 ml (1387 g) of 1,3-divinyl-1,1,3,3-tetramethyl-disiloxane (obtainable as Wacker Siloxan VSi2 from Wacker Chemie AG, Munich, Germany) and 550 ml of concentrated hydrochloric acid before the reaction mixture was stirred at room temperature for 7 days. The phases were then separated, the organic phase was washed neutral with water, dried over sodium sulfate and completely evaporated. The residue was recrystallized from ethanol to obtain 64 g of a crystalline substance (69% of theory, based on silica used), which was shown by measurements based on vapor pressure osmometry to have a molar mass of 1120 g·$mol^{-1}$. The gel permeation chromatography (GPC) diagram is indicative of a unitary compound. The $^1H$ and $^{29}Si$ NMR and IR data are in agreement with the structure of octa(vinyldimethylsiloxy)octasilsesquioxane.

Example 2 (Corresponds to Example 9 of DE 38 37 397 A1, and is Not in Accordance with the Present Invention)

Synthesis of octa(dimethylsiloxy)octasilsesquioxane $[H(CH_3)_2SiOSiO_{3/2}]_8$ 160 g of the tetramethylammonium silicate produced as per Example 1a) were added a little at a time to an efficiently stirred mixture of 400 ml of $H_2O$, 1000 ml of isopropanol, 1500 ml (1136 g) of 1,1,2,2-tetramethyl-disiloxane (obtainable as Wacker Siloxan HSi2 from Wacker Chemie AG, Munich, Germany) and 200 ml of 10% strength hydrochloric acid before the reaction mixture was stirred at room temperature for 4 hours.

The rest of the workup was carried out as described in Example 1b). The silylation product obtained was recrystallized from acetone.

This gave 52.0 g of a crystalline substance (67% of theory, based on silica used), which was shown by measurements based on vapor pressure osmometry to have a molar mass of 1150 g·mol$^{-1}$. The GPC diagram is indicative of a unitary compound. The $^1H$ and $^{29}Si$ NMR and IR data are in agreement with the structure of octa(dimethylsiloxy)octasilsesquioxane. Active hydrogen content: theory: 0.79% by weight, found: 0.75% by weight.

Example 3 (in Accordance with the Present Invention)

Synthesis of octa(vinyldimethylsiloxy)octasilsesquioxane [($H_2C$=CH) ($CH_3$)$_2$SiOSiO$_{3/2}$]$_8$ a) Production of silicate base: 151 g of a 25% strength aqueous TMAOH solution were initially charged to a 2 liter three-neck flask equipped with dropping funnel and reflux condenser and also magnetic stirrer together with 226 g of methanol. 85.36 g of tetraethoxysilane (obtainable as TES 28 from Wacker Chemie AG, Munich, Germany) were added to the initial charge over a period of 75 minutes. Following a subsequent stirring time of 2-4 h, this reaction mixture, which contained tetramethylammonium silicate, could be used as such for the next process step, the silylation.

b) Silylation (precipitation reaction)

A 4 liter three-neck glass flask equipped with dropping funnel and reflux condenser and also magnetic stirrer was initially charged with 100 g of 1,3-divinyl-1, 1,3,3-tetramethyldisiloxane (obtainable as Wacker Siloxan VSi2 from Wacker Chemie AG, Munich, Germany), 390.5 g of isopropyl alcohol, 150 g of HCl (20% strength) and 50 g of $H_2O$ (completely ion-free water). Under constant agitation, the mixture described under a), which contained tetramethylammonium silicate, was added to the initial charge in the course of 80-100 minutes.

Following a subsequent stirring time of 2-4 h, the resulting product had settled out on the glass bottom and was separated from the liquid phase using suction filtration.

The crystalline product thus separated off was washed with completely ion-free water (about 100 g) and dried at 100° C. in a drying cabinet.

This gave 42.4 g of a crystalline substance (=71% yield based on silica used).

GPC was used to measure a unitary molar mass of 1171.7 g/mol, with $M_n$ and $M_w$ being the same and the compound obtained thus having a polydispersity of 1.0. $^1H$ and $^{29}Si$ NMR data are in agreement with the structure of octa(vinyldimethylsiloxy)octasilsesquioxane.

Example 4 (in Accordance with the Present Invention)

Synthesis of octa(dimethylsiloxy)octasilsesquioxane [H($CH_3$)$_2$SiOSiO$_{3/2}$]$_8$ a) Silicate production was carried out as in Example 3 a).
b) Silylation (precipitation reaction)

A 4 liter three-neck glass flask equipped with dropping funnel and reflux condenser and also magnetic stirrer was initially charged with 60.5 g of 1,1,3,3-tetramethyldisiloxane (obtainable as Wacker Siloxan HSi2 from Wacker Chemie AG, Munich, Germany), 390.5 g of isopropyl alcohol, 150 g of HCl (20% strength) and 100 g of $H_2O$ (completely ion-free water).

Under constant agitation, the mixture described under A, which contained tetramethylammonium silicate, was added to the initial charge in the course of 80-100 minutes.

Following a subsequent stirring time of 2-4 h, the resulting product had settled out on the glass bottom and was separated from the liquid phase using suction filtration.

The crystalline product thus separated off was washed with completely ion-free water (about 100 g) and dried at 100° C. in a drying cabinet.

This gave 45 g of a crystalline substance (=86.3% yield based on silica used).

GPC was used to measure a unitary molar mass of 1032.29 g/mol, with $M_n$ and $M_w$ being the same and the compound obtained thus having a polydispersity of 1.0. $^1H$ and $^{29}Si$ NMR data are in agreement with the structure of octa(vinyldimethylsiloxy)octasilsesquioxane. In addition, the active hydrogen content of 0.79% by weight as per $^1H$ NMR analysis is equal to the theohretical value (0.79% by weight).

The invention claimed is:

1. A method for producing organooligosilsesquioxanes of the formula (I)

$$[RSiO_{3/2}]_z \quad (I)$$

where
R represents moieties of general formula (II)

$$-O-SiR^1_2Y \quad (II),$$

by reacting of silicates of formula (III)

$$(W_4NOSiO_{3/2})_z \quad (III),$$

with not more than 1.3×50×z mol of disiloxane compounds of general formula (IV), $$R^1_2YSi-O-SiR^1_2Y \quad (IV),$$

per 100 mol of the silicates of the formula (III),
wherein
R$^1$ independently are divalent C$_1$- to C$_6$-hydrocarbon or C$_1$- to C$_6$-alkoxy moieties,
Y independently are hydrogen or a halogenated or nonhalogenated C$_1$- to C$_{10}$-hydrocarbon moiety,
W is a C$_1$- to C$_4$-alkyl moiety, and
z is 6, 8 or 10,
reacting taking place in the presence of a precipitant which is liquid at 25° C. and 0.1 Mpa and in which at a reaction temperature of 0° C. to 60° C., at most 1 g of organooligosilsesquioxanes of formula (I) are soluble in 100 ml of precipitant, wherein the resultant organooligosilsesquioxane of formula (I) crystallizes out in the reaction medium at a purity of 95-100%, measured via $^1H$ NMR, during the reaction or directly after the reaction.

2. The method of claim 1, wherein R$^1$ is selected from the group consisting of methyl, ethyl, phenyl, methoxy, ethoxy, propoxy, and mixtures thereof 3. The method of claim 1, wherein Y is selected from the group consisting of methyl, phenyl, C$_2$- to C$_{10}$-alkenyl, C$_1$- to C$_{10}$-alkyl moieties having a halogen atom on a terminal carbon atom, and mixtures thereof.

4. The method of claim 2, wherein Y is selected from the group consisting of methyl, phenyl, C$_2$- to C$_{10}$-alkenyl, C$_1$- to $C_{10}$-alkyl moieties having a halogen atom on a terminal carbon atom, and mixtures thereof.

5. The method of claim 1, wherein W is selected from methyl, ethyl, n-propyl, and mixtures thereof 6. The method of claim 2, wherein W is selected from methyl, ethyl, n-propyl, and mixtures thereof 7. The method of claim 3, wherein W is selected from methyl, ethyl, n-propyl, and mixtures thereof 8. The method of claim 1, wherein the precipitant is polar and is selected from the group consisting of water, alcohols, ethers, chlorinated hydrocarbons, ketones, nitriles, nitro compounds, tertiary carboxamides, urea derivatives, sulfoxides, carbonic esters, carbon sulfide, carboxylic acids, mineral acids, and mixtures thereof 9. The method of claim 2, wherein the precipitant is polar and is selected from the group consisting of water, alcohols, ethers, chlorinated hydrocarbons, ketones, nitriles, nitro compounds, tertiary carboxamides, urea derivatives, sulfoxides, carbonic esters, carbon sulfide, carboxylic acids, mineral acids, and mixtures thereof 10. The method of claim 3, wherein the precipitant is polar and is selected from the group consisting of water, alcohols, ethers, chlorinated hydrocarbons, ketones, nitriles, nitro compounds, tertiary carboxamides, urea derivatives, sulfoxides, carbonic esters, carbon sulfide, carboxylic acids, mineral acids, and mixtures thereof 11. The method of claim 4, wherein the precipitant is polar and is selected from the group consisting of water, alcohols, ethers, chlorinated hydrocarbons, ketones, nitriles, nitro compounds, tertiary carboxamides, urea derivatives, sulfoxides, carbonic esters, carbon sulfide, carboxylic acids, mineral acids, and mixtures thereof 12. The method of claim 1 wherein, in a first step, silicates of formula (III) are produced in a solution of $W_4N^+OH^-$ in the precipitant with tetraalkoxysilanes where the alkoxy moieties have 1 to 6 carbon atoms, and the mixture thus produced is then used directly as a crude reaction mixture to react with the disoloxane compounds of the formula (IV).

\* \* \* \* \*